United States Patent [19]

Mansour et al.

[11] Patent Number: 5,512,569
[45] Date of Patent: Apr. 30, 1996

[54] AMINOALKYL BENZOTHIAZOLINONES

[75] Inventors: Hamid A. Mansour, Roubaix; Thierry Taverne, Saint Martin Les Boulogne; Raymond Houssin, Marq-En-Baroeul; Isabelle Lesieur, Gondecourt; Patrick Depreux, Armentieres; Géard Adam, Le Mesnil Le Roi; Daniel-Henri Caignard, Paris; Pierre Renard, Versailles; Marie-Claire Rettori, Courbevoie, all of France

[73] Assignee: Adir et Compagnie, Courbevoie, France

[21] Appl. No.: 408,069

[22] Filed: Mar. 21, 1995

[30] Foreign Application Priority Data

Mar. 22, 1994 [FR] France .................. 94 03299
Mar. 22, 1994 [FR] France .................. 94 03300

[51] Int. Cl.$^6$ .............. A61K 31/495; A61K 31/535; C07D 417/02
[52] U.S. Cl. .............. 514/233.8; 514/212; 514/228.2; 514/253; 514/321; 514/367; 540/603; 544/58.7; 544/135; 544/368; 546/198; 548/165
[58] Field of Search .............. 544/135, 368; 548/165; 514/367, 233.8

[56] References Cited

U.S. PATENT DOCUMENTS 5,268,381  12/1993  Taverne et al. .............. 548/165

FOREIGN PATENT DOCUMENTS 281309  9/1988  European Pat. Off. ..
366511  5/1990  European Pat. Off. ..
385848  9/1990  European Pat. Off. ..
478446  4/1992  European Pat. Off. ..

OTHER PUBLICATIONS

Kaiser et al., Neurotransmissions, VII 1991, pp. 1–4.
Martindale, The Extra Pharmacopia, 30th Edition, pp. 567–568.
Z. Moussavi et al., Farmaco, Edizione Pratica, 44 (1) 1989, pp. 77–88.
J. Lowe et al., Journal of Medicinal Chemistry, "1–Naphthylpiperazine Derivatives As Potential Atyptical Antipsychotic Agents", 34 (6) 1991, pp. 1860–1866.

Primary Examiner—Robert W. Ramsuer
Attorney, Agent, or Firm—Gordon W. Hueschen

[57] ABSTRACT

The invention relates to the compounds of formula (I):

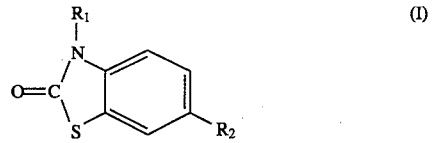

in which $R_1$ and $R^2$ are as defined in the description,
the optical isomers thereof,
and an addition salt thereof with a pharmaceutically-acceptable acid or base, and medicinal product useful for treating a mammal afflicted with a disease associated with sigma receptors.

10 Claims, No Drawings

AMINOALKYL BENZOTHIAZOLINONES

The present invention relates to novel aminoalkyl benzothiazolinones, to a process for their preparation and to the pharmaceutical compositions which contain them.

Patent Application EP 478,446 describes (aminoalkyl-)benzothiazolinone compounds as antipsychotic, analgesic and anxiolytic agents.

The Applicant has now discovered novel aminoalkyl benzothiazolinones which possess, surprisingly, a much more intense affinity for the sigma ($\sigma$) receptors than do the compounds of Application EP 478,446.

The very high affinity of the compounds of the invention for the sigma s receptors, which is considerably greater than that obtained with the compounds of Application EP 478,446, makes it possible for them to be used in the prevention and treatment of diseases associated with receptors of this type, namely psychiatric diseases, psychosis, schizophrenia, depression, stress, anxiety, cerebral circulatory insufficiency, memory disorders and Alzheimer's disease, as well as inflammatory diseases of immune type, acute arthritis or chronic arthritis and intestinal peristaltis disorders.

Moreover, the high selectivity of the compounds of the present invention for the sigma receptors, in particular their absence of affinity for the $D_2$ receptors, allows them to be used therapeutically with increased safety. In particular, the side effects of extrapyramidal type which are encountered during treatment with products having a high $D_2$ component, to which these effects are attributed, are not found with the products of the invention which have, on average, 100 to 1000 times less affinity for the $D_2$ receptors than do the compounds of Application EP 478,446. On balance, the products of the present invention have a selectivity ratio (sigma receptor affinity): ($D_2$ receptor affinity) which is 10,000 to 100,000 times greater than that obtained with the compounds of Application EP 478,446, which is totally unexpected in view of Application EP 478,446, thereby considerably enhancing their safety of use.

The present invention relates more particularly to the compounds of formula (I):

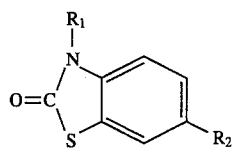

in which:

R$_1$ represents a hydrogen or an alkyl or substituted alkyl radical, and R$_2$ represents a group of formula R$_{21}$:

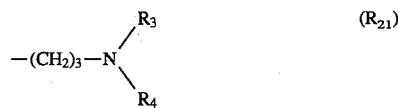

in which:

R$_3$ and R$_4$ represent, independently of each other, a hydrogen atom or a radical chosen from alkyl, cycloalkyl, cycloalkylalkyl, alkenyl, alkynyl and —(CH$_2$)$_m$-aryl; with m representing 0, 1, 2, 3 or 4, the aryl group possibly being unsubstituted or substituted, or alternatively R$_3$ and R$_4$ together form a saturated 5- to 9-membered heterocycle which may contain other hetero atoms chosen from oxygen and sulfur and which may be unsubstituted or substituted or 4-(methoxyphenyl)-piperazin-1-yl, or a group of formula R$_{22}$:

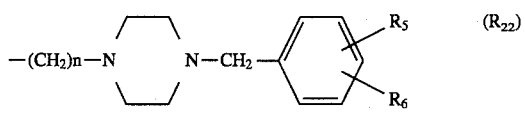

in which n represents 2, 3 or 4, and R$_5$ and R$_6$, which are identical, represent a hydrogen or a halogen, it being understood that in the description of the formula (I), the term "substituted" associated with the "aryl" radical means that the substitution may be made by one or more radicals chosen from halogen, hydroxyl, alkyl, lower alkoxy and alkyl which is substituted with one or more halogens, the term "substituted" associated with the heterocycle formed by —NR$_3$R$_4$ means that the substitution may be made by one or more alkyl radicals, the terms "alkyl" and "alkoxy" denote linear or branched groups containing from 1 to 6 carbon atoms, the terms "alkenyl" and "alkynyl" denote linear or branched groups of 2 to 6 carbon atoms, the term "aryl" means phenyl or naphthyl, and the term "cycloalkyl" represents a cyclic group of 3 to 8 carbon atoms, the optical isomers thereof and the addition salts thereof with a pharmaceutically acceptable acid or, when R$_1$ represents a hydrogen, the addition salts thereof with a pharmaceutically acceptable base.

The invention relates particularly to the compounds of formula (I) in which R$_2$ represents a group of formula R$_{21}$ and R$_3$ and R$_4$ form, together with the nitrogen atom which bears them, a group chosen from morpholino, thiomorpholino, pyrrolidino, piperidino and perhydroazepino, for example morpholino.

The invention particularly relates to the compounds of formula (I) in which R$_2$ represents a group of formula R$_{22}$ and R$_5$ and R$_6$, which are identical, represent a chlorine.

Among the pharmaceutically acceptable acids which may be used to form an addition salt with the compounds of the invention, non-limiting examples which may be mentioned are hydrochloric acid, sulfuric acid, phosphoric acid, tartaric acid, malic acid, maleic acid, fumaric acid, oxalic acid, methanesulfonic acid, ethanesulfonic acid, camphoric acid and citric acid.

Among the pharmaceutically acceptable bases which may be used to form an addition salt with the compounds of the invention, non-limiting examples which may be mentioned are sodium hydroxide, potassium hydroxide, calcium hydroxide or aluminum hydroxide, alkali metal or alkaline-earth metal carbonates and organic bases such as triethylamine, benzylamine, diethanolamine, tert-butylamine, dicyclohexylamine and arginine.

The alkyl radicals present in formula (I) may specifically be chosen from methyl, ethyl, n-propyl, isopropyl, n-butyl, isobutyl, sec-butyl, tert-butyl, pentyl or hexyl.

The alkoxy radicals present in formula (I) may be chosen from methoxy, ethoxy, n-propoxy, isopropoxy, n-butoxy, isobutoxy, sec-butoxy, tert-butoxy, pentyloxy and hexyloxy.

The halogens present in formula (I) may be chosen from bromine, chlorine, fluorine and iodine.

The cycloalkyls present in the substituents of formula (I) may be chosen from cyclopropyl, cyclobutyl, cyclopentyl, cyclohexyl, cycloheptyl and cyclooctyl.

The invention also covers the process for the preparation of the compounds of formula (I) in which a compound of formula (II) is introduced into a suitable solution:

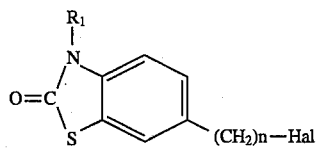

in which $R_1$ and n are as defined in formula (I) and Hal is a halogen atom, which compound is condensed:
either with a compound of formula (III/a):

in which $R_5$ and $R_6$ are as defined in formula (I),
to give the compounds of formula (I/a):

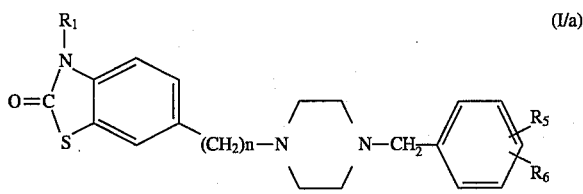

in which $R_1$, $R_5$, $R_6$ and n are as defined above,
or, when n is equal to 3, with a compound of formula (III/b):

in which $R_3$ and $R_4$ are as defined in formula (I),
to give a compound of formula (I/b):

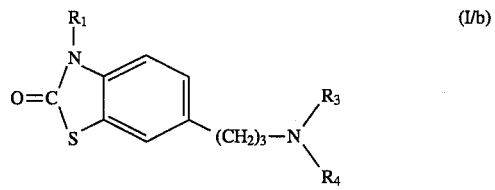

in which $R_1$, $R_3$ and $R_4$ are as defined above,
the compounds of formulae (I/a) and (I/b) together forming compounds of formula (I), which compounds of formula (I) are, if so desired, separated, if necessary, into the various optical isomers thereof or are salified with a pharmaceutically acceptable acid or, if $R_1$ represents a hydrogen atom, are salified with a pharmaceutically acceptable base.

The starting materials used in the process described above are either commercial or are readily accessible to those skilled in the art according to processes which are well known in the literature. For the compounds of formula (II), reference will be made more particularly to the description of Patent Application EP 430,800.

The compounds of formula (I) possess advantageous pharmacological properties.

The very high affinity of the compounds of the invention for the σ receptors makes it possible for them to be used in the treatment of motor disorders, dystonia (Walker, JM: Drug specificity of pharmacology dystonia, Pharmacol. Biochem. Behav. 1990, 36, 151), tardive dyskinesia (Lindstrom, L. H.: Acta Psychiatr. Scand. 1988, 77, 1122), psychotic disorders (Chouinard, F., Annable, L. Psychopharmacology 1984, 84, 282), and in the treatment of damage associated with peripheral or cerebral ischemia, cerebral circulatory insufficiency, memory disorders, Alzheimer's disease and states of shock (Pontecorvo, M. J., Brain Res. Bull. 1991, 26, 461), in the regulation of immune phenomena (Carroll, F. I., Med. Chem. Res. 1992, 2, 3), the treatment of addiction to cocaine (Abou-Gharbia, M., Academic. Press. Inc. Bristol. J. Ed. Publisher. 1993, 28, 1), the diagnosis and localization of tumors (Hudzik, T. J., Psychopharmacology. 1992, 108, 115; Abou-Gharbia, M., Academic. Press. Inc. Bristol. J. Ed. Publisher 1993, 28, 1) and vomiting (Hudzik, T. J., Eur. J. Pharmacol. 1993, 236, 279), as well as in the treatment of inflammatory diseases of immune origin and intestinal motility disorders.

A subject of the present invention is also the pharmaceutical compositions containing the compounds of formula (I) or one of the addition salts thereof with a pharmaceutically acceptable acid or, where appropriate, a pharmaceutically acceptable base, in combination with one or more excipients.

Among the pharmaceutical compositions according to the invention, mention may more particularly be made of those which are suitable for oral, parenteral, nasal, percutaneous or transcutaneous, rectal, perlingual, ocular or respiratory administration and especially simple or sugar-coated tablets, sublingual tablets, sachets, packets, gelatin capsules, glossettes, lozenges, suppositories, creams, ointments, dermal gels and drinkable or injectable ampules.

The dosage varies depending on the sex, age and weight of the patient, the route of administration, the nature of the therapeutic indication, or on treatments which are possibly associated, and is graduated between 0.1 mg and 1 g taken once or twice per 24 hours, more particularly 1 to 100 mg, for example 1 to 10 mg.

The examples which follow illustrate the invention.

The $^1$H nuclear magnetic resonance spectra were acquired using TMS (tetramethylsilane) as internal reference. The chemical shifts are expressed in parts per million (ppm). The infrared spectra were acquired in the form of potassium bromide pastilles containing approximately 1% of the product to be analyzed.

The preparations do not form part of the invention, but are useful for performing the synthesis of the compounds of the invention.

PREPARATION 1

6-(3-Chloropropionyl)benzothiazolinone

Reactants:
Benzothiazolinone: 0.05 mol (7.55 g)
3-Chloropropionyl chloride: 0.05 mol (4.77 cm$^3$)
Aluminum chloride: 0.40 mol (52.50 g)
Anhydrous dimethylformamide: 0.12 mol (9.20 cm$^3$)
Procedure:

0.40 mol of aluminum chloride is introduced into a ground-necked flask on which is fitted a water-condenser, followed by dropwise addition of 0.12 mol of anhydrous dimethylformamide with magnetic stirring.

0.05 mol of benzothiazolinone is added and the temperature is stabilized at 70° C. The medium is thoroughly homogenized and 0.05 mol of 3-chloropropionyl chloride is added slowly.

After addition, the mixture is left stirring for one hour at 70° C. The medium is poured onto crushed ice and drained, and the precipitate formed is washed with water until the washing waters are neutral, then it is dried and recrystallized.
Molecular weight: 241.69 g.mol$^{-1}$ for $C_{10}H_8ClNO_2S$
Melting point: 174°–177° C. (decomposition)
Yield: 55%
Recrystallization solvent: Absolute ethanol

PREPARATION 2

6-(3-Chloropropyl)benzothiazolinone

Reactants:
6-(3-Chloropropionyl)benzothiazolinone: 0.10 mol (24.16 g)
Trifluoroacetic acid: 0.80 mol (61.60 cm$^3$)
Triethylsilane: 0.20 mol (32.00 cm$^3$)
Procedure:

0.1 mol of 6-(3-chloropropionyl)benzothiazolinone is dissolved in 0.8 mol of trifluoroacetic acid in a 250 cm$^3$ ground-necked flask. 0.2 mol of triethylsilane is introduced dropwise and with magnetic stirring, by means of a dropping funnel.

A calcium chloride guard tube is fitted and stirring is continued at room temperature for the required time.

The reaction mixture is poured into 500 cm$^3$ of ice-water.

The precipitate obtained is drained, washed with water until the washing waters are neutral, dried and then recrystallized.
Reaction time: 50 hours
Molecular weight: 227.71 g.mol$^{-1}$ for $C_{10}H_{10}ClNOS$
Melting point: 131°–133° C.
Yield: 86%
Recrystallization solvent: toluene

PREPARATION 3

3-Methyl-6-(3-Chloropropyl)benzothiazolinone

Reactants:
3-Methylbenzothiazolinone: 0.05 mol (8.25 g)
3-Chloropropionyl chloride: 0.06 mol (5.72 cm3)
Aluminum chloride: 0.40 mol (52.50 g)
Dimethylformamide: 0.20 mol (9.20 cm3)
Procedure:

The procedure is identical to that used to obtain 6-(3-chloropropionyl)benzothiazolinone, replacing benzothiazolinone by 3-methyl benzothiazolinone.
Molecular weight: 237.27 g.mol$^{-1}$ for $C_{11}H_{10}ClNO_2S$
Melting point: 174°–177° C.
Yield: 60%
Recrystallization solvent: Absolute ethanol

PREPARATION 4

3-Methyl-6-(3-Chloropropyl)benzothiazolinone

Reactants:
3-Methyl-6-(3-chloro-propionyl) benzothiazolinone: 0.1 mol (23.72 g)
Trifluoroacetic acid: 0.8 mol (61.60 cm3)
Triethylsilane: 0.2 mol (32.00 cm3)
Procedure:

The procedure is identical to that used to obtain 6-(3-chloropropyl)benzothiazolinone, replacing 6-(3-chloropropionyl)benzothiazolinone by 3-methyl-6-(3-chloropropionyl)benzothiazolinone.
Reaction time: 72 hours
Molecular weight: 241.73 g.mol$^{-1}$ for $C_{11}H_{12}ClNOS$ Melting point: 41°–43° C.
Yield: 84%
Recrystallization solvent: Cyclohexane

EXAMPLE 1

6-(3-Morpholinopropyl)benzothiazolinone

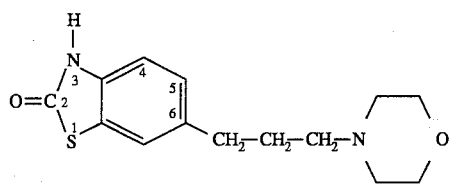

(Example 1)

0.02 mol (4.55 g) of 6-(3-chloropropyl)benzothiazolinone, 0.03 mol (2.60 cm$^3$) of morpholine and 0.03 mol (4.20 cm$^3$) of triethylamine are introduced into 80 cm$^3$ of absolute alcohol contained in a 250 cm$^3$ ground-necked flask fitted with a condenser.

The mixture is heated at reflux for thirty hours. The triethylamine hydrochloride precipitate is drained off and the filtrate is then evaporated on a water bath, at reduced pressure. The residue is taken up in aqueous 1N hydrochloric acid solution and is extracted with ether.

The aqueous phase is basified with 10% sodium hydroxide solution. It is extracted twice with ether and the ether phases are combined, dried over calcium chloride, filtered and evaporated under reduced pressure.

The residue is taken up in anhydrous ether and sparged with gaseous hydrogen chloride, and the precipitate formed is drained and recrystallized. The title compound is obtained in the form of the hydrochloride.
Molecular weight 314.83 g.mol$^{-1}$ for $C_{14}H_{19}ClN_2O_2S$
Yield: 62%
Melting point: 239°–241° C.
Recrystallization solvent: Absolute alcohol

| Elemental analysis: | | | |
|---|---|---|---|
|  | % C | % H | % N |
| Calculated: | 54.40 | 6.08 | 8.89 |
| Found: | 54.33 | 5.86 | 8.72 |

| Infrared spectrometry: | | |
|---|---|---|
| 2920 | cm$^{-1}$ | ν CH (alkyls) |
| 2660–2450 | cm$^{-1}$ | ν NH$^+$ (hydrochloride) |
| 1690 | cm$^{-1}$ | ν CO (NCOS) |
| 1600 | cm$^{-1}$ | ν C=C (aromatics) |

| Nuclear magnetic resonance spectrometry (80 MHz; DMSO-d$_6$): | | | |
|---|---|---|---|
| δ = 2.20 | ppm | (multiplet, 2H) | CH$_2$—<u>CH$_2$</u>—CH$_2$ |
| δ = 2.70 | ppm | (triplet, 2H) | Benzothiazolinone-<u>CH$_2$</u> |
| δ = 7.00 | ppm | (singlet, 2H) | H$_{4,5}$ (benzothiazolinone) |
| δ = 7.40 | ppm | (singlet, 1H) | H$_7$ (benzothiazolinone) |
| δ = 11.80 | ppm | (peak, 2H) | NH,NH$^+$ exchangeable in D$_2$O |

EXAMPLE 2

3-Methyl-6-(3-Morpholinopropyl)benzothiazolinone

Reactants:
3-Methyl-6-(3-chloropropyl)benzothiazolinone: 0.02 mol (4.83 g)

Morpholine: 0.03 mol (2.60 cm³)
Triethylamine: 0.03 mol (4.20 cm³)
Anhydrous acetone: 60 cm³
Procedure:

The procedure is identical to that used in Example 1, replacing 6-(3-chloropropyl)benzothiazolinone by 3-methyl-6-(3-chloropropyl)benzothiazolinone.
Molecular weight: 328.86 g.mol⁻¹ for $C_{15}H_{21}ClN_2O_2S$
Yield: 67%
Melting point (hydro-chloride): 210°–212° C.
Recrystallization solvent: Absolute alcohol

| Elemental analysis: | | | |
| --- | --- | --- | --- |
| | % C | % H | % N |
| Calculated: | 54.78 | 6.43 | 8.52 |
| Found: | 54.76 | 6.70 | 8.70 |

| Infrared spectrometry: | | |
| --- | --- | --- |
| 2900 | cm⁻¹ | ν CH (alkyls) |
| 2660–2450 | cm⁻¹ | ν NH⁺ (hydrochloride) |
| 1670 | cm⁻¹ | ν CO (NCOS) |
| 1600 | cm⁻¹ | ν C=C (aromatics) |

| Nuclear magnetic resonance spectrometry (80 MHz; DMSO-d6): | | | |
| --- | --- | --- | --- |
| δ = 2.10 | ppm | (multiplet, 2H) | CH₂—C$\underline{H_2}$—CH₂ |
| δ = 2.75 | ppm | (triplet, 2H) | Benzothiazolinone-C$\underline{H_2}$ |
| δ = 3.40 | ppm | (singlet, 3H) | NCH₃ |
| δ = 3.90 | ppm | (multiplet, 4H) | C$\underline{H_2}$—O—C$\underline{H_2}$ |
| δ = 7.35 | ppm | (multiplet, 3H) | H$_{4,5,7}$ (benzothiazolinone) |
| δ = 11.20 | ppm | (peak, 1H) | NH⁺ exchangeable in D₂O |

EXAMPLE 3

6-[3-(3,5-Dimethyl)morpholinopropyl]benzothiazolinone

By working in the same manner as in Example 1, but replacing the morpholine by 3,5-dimethylmorpholine, the title compound is obtained.

EXAMPLE 4

3-Methyl-6-[3-(3,5-Dimethyl)Morpholinopropyl]Benzothiazolinone

By working in the same manner as in Example 2, but replacing the morpholine by 3,5-dimethylmorpholine, the title compound is obtained.

EXAMPLE 5

6-(3-Piperid-1-yl-propyl)benzothiazolinone

By working in the same manner as in Example 1, but replacing the morpholine by piperidine, the title compound is obtained.

EXAMPLE 6

3-Methyl-6-(3-Piperid-1-yl-propyl)benzothiazolinone

By working in the same manner as in Example 2, but replacing the morpholine by piperidine, the title compound is obtained.

EXAMPLE 7

6-(3-Pyrrolidin-1-yl-propyl)benzothiazolinone

By working in the same manner as in Example 1, but replacing the morpholine by pyrrolidine, the title compound is obtained.

EXAMPLE 8

3-Methyl-6-(3-pyrrolidin-1-yl-propyl)benzothiazolinone

By working in the same manner as in Example 2, but replacing the morpholine by pyrrolidine, the title compound is obtained.

EXAMPLE 9

6-(3-N,N-dipropylaminopropyl)benzothiazolinone

By working in the same manner as in Example 1, but replacing the morpholine by N,N-dipropylamine, the title compound is obtained.

EXAMPLE 10

3-Methyl-6-(3-N,N-dipropylaminopropyl)benzothiazolinone

By working in the same manner as in Example 2, but replacing the morpholine by N,N-dipropylamine, the title compound is obtained.

EXAMPLE 11

6-(3-N-cyclohexylaminopropyl)benzothiazolinone

By working in the same manner as in Example 1, but replacing the morpholine by cyclohexylamine, the title compound is obtained.

EXAMPLE 12

3-Methyl-6-(3-N-cyclohexylaminopropyl)benzothiazolinone

By working in the same manner as in Example 2, but replacing the morpholine by cyclohexylamine, the title compound is obtained.

EXAMPLE 13

6-(3-Benzylaminopropyl)benzothiazolinone

By working in the same manner as in Example 1, but replacing the morpholine by benzylamine, the title compound is obtained.

EXAMPLE 14

3-Methyl-6-(3-benzylaminopropyl)benzothiazolinone

By working in the same manner as in Example 2, but replacing the morpholine by benzylamine, the title compound is obtained.

EXAMPLE 15

6-[3-(4-Methoxybenzyl)aminopropyl)benzothiazolinone

By working in the same manner as in Example 1, but replacing the morpholine by 4-methoxybenzylamine, the title compound is obtained.

EXAMPLE 16

3-Methyl-6-[3-(4-Methoxybenzyl)aminopropyl) benzothiazolinone

By working in the same manner as in Example 2, but replacing the morpholine by 4-methoxybenzylamine, the title compound is obtained.

EXAMPLE 17

6-{3-[1-(Naphth-1-yl)ethylamino] propyl}benzothiazolinone

By working in the same manner as in Example 1, but replacing the morpholine by 1-(1-naphthyl)ethylamine, the title compound is obtained.

EXAMPLE 18

3-Methyl-6-{3-[1-(Naphth-1-yl)ethylamino]propyl} benzothiazolinone

By working in the same manner as in Example 2, but replacing the morpholine by 1-(1-naphthyl)ethylamine, the title compound is obtained.

EXAMPLE 19

6-[3-(4-Methylbenzyl)aminopropyl]benzothiazolinone

By working in the same manner as in Example 1, but replacing the morpholine by 4-methylbenzylamine, the title compound is obtained.

EXAMPLE 20

3-Methyl-6-[3-(4-Methylbenzyl)aminopropyl] benzothiazolinone

By working in the same manner as in Example 2, but replacing the morpholine by 4-methylbenzylamine, the title compound is obtained.

EXAMPLE 21

6-[3-(4-Trifluoromethylbenzyl)aminopropyl] benzothiazolinone

By working in the same manner as in Example 1, but replacing the morpholine by 4-trifluoromethylbenzylamine, the title compound is obtained.

EXAMPLE 22

3-Methyl-6-[3-(4-Trifluoromethylbenzyl)aminopropyl benzothiazolinone

By working in the same manner as in Example 2, but replacing the morpholine by 4-trifluoromethylbenzylamine, the title compound is obtained.

EXAMPLE 23

6-[3-(3,4-Dichlorobenzyl)aminopropyl] benzothiazolinone

By working in the same manner as in Example 1, but replacing the morpholine by 3,4-dichlorobenzylamine, the title compound is obtained.

EXAMPLE 24

3-Methyl-6-[3-(3,4-Dichlorobenzyl)aminopropyl] benzothiazolinone

By working in the same manner as in Example 2, but replacing the morpholine by 3,4-dichlorobenzylamine, the title compound is obtained.

EXAMPLE 25

6-(3-Thiomorpholinopropyl)benzothiazolinone

By working in the same manner as in Example 1, but replacing the morpholine by thiomorpholine, the title compound is obtained.

EXAMPLE 26

3-Methyl-6-(3-Thiomorpholinopropyl) benzothiazolinone

By working in the same manner as in Example 2, but replacing the morpholine by thiomorpholine, the title compound is obtained.

EXAMPLE 27

3-Methyl-6-(3-Allylaminopropyl)benzothiazolinone

By working in the same manner as in Example 2, but replacing the morpholine by allylamine, the title compound is obtained.

EXAMPLE 28

3-Methyl-6-[2-(4-Benzylpiperazin-1-yl)ethyl] benzothiazolinone

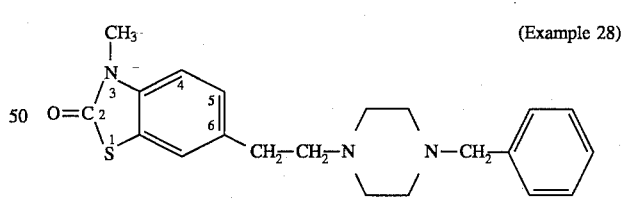
(Example 28)

Reactants:
3-Methyl-6-(2-bromoethyl)benzothiazolinone: 0.0074 mol (2 g)
4-Benzylpiperazine: 0.0074 mol (1.30 cm$^3$)
Potassium carbonate: 0.029 mol (4 g)
Anhydrous dimethylformamide: 50 cm$^3$ Procedure:
  0.0074 mol of 4-benzylpiperazine and 0.029 mol of potassium carbonate are introduced into 30 cm$^3$ of anhydrous dimethylformamide contained in a 250 cm$^3$ ground-necked flask fitted with a condenser. The mixture is heated at reflux for 30 minutes, followed by addition of 0.0074 mol of 3-methyl-6-(2-bromoethyl)benzothiazolinone dissolved in 20 cm$^3$ of dimethylformamide.

The reaction mixture is heated for 12 hours. It is allowed to cool and the inorganic precipitate is drained off. The filtrate is poured into 30 cm³ of distilled water and is acidified. This mixture is left stirring for 30 minutes and is then extracted with ethyl acetate in order to remove the residual starting material. The aqueous phase is immediately basified.

The organic phase is extracted with ethyl acetate. The organic fractions are combined and are all dried, filtered and then evaporated on a water bath, under reduced pressure.

The residue is taken up in 50 cm³ of absolute alcohol and sparged with gaseous hydrogen chloride, and the precipitate formed is drained and recrystallized. The title compound is obtained in the form of the dihydrochloride.
Molecular weight: 440.36 g.mol⁻¹ for $C_{21}H_{27}Cl_2N_3OS$
Yield: 45%
Melting point: >270° C.
Recrystallization solvent: Absolute alcohol Elemental analysis:

|  | % C | % H | % N |
|---|---|---|---|
| Calculated | 57.27 | 6.18 | 9.54 |
| Found | 57.31 | 6.15 | 9.50 |

Infrared spectrometry:

| 2900 | cm⁻¹ | ν CH (alkyls) |
|---|---|---|
| 2340 | cm⁻¹ | ν NH+ (hydrochloride) |
| 1690 | cm⁻¹ | ν CO (NCOS) |
| 1600 | cm⁻¹ | ν C=C (aromatics) |

Nuclear magnetic resonance spectrometry (80 MHz; DMS-d₆):

| $\delta$ = 2.80–3.14 | ppm | (multiplet, 12H) | ethyl and piperazine |
|---|---|---|---|
| $\delta$ = 3.40 | ppm | (singlet, 3H) | NCH₃ |
| $\delta$ = 4.10 | ppm | (singlet, 2H) | CH₂—C₆H₅ |
| $\delta$ = 7.20–7.70 | ppm | (multiplet, 8H) | aromatic H |
| $\delta$ = 11.00 | ppm | (peak, 2H) | 2NH+ exchangeable in D₂O |

EXAMPLE 29

3-Methyl-6-[4-(4-benzylpiperazin-1-yl)butyl] benzothiazolinone

Reactants:
3-Methyl-6-(4-bromobutyl)benzothiazolinone: 0.01 mol (3 g)
4-Benzylpiperazine: 0.01 mol (1.80 cm³)
Potassium carbonate: 0.04 mol (5.5 g)
Anhydrous dimethylformamide: 45 cm³
Procedure:
The procedure is identical to that used in Example 28, replacing 3-methyl-6-(2-bromoethyl)benzothiazolinone by 3-methyl-6-(4-bromobutyl)benzothiazolinone.
Physicochemical data for the dihydrochloride:
Molecular weight: 468.42 g.mol⁻¹ for $C_{23}H_{31}Cl_2N_3OS$
Yield: 55%
Melting point: >250° C.
Recrystallization solvent: Absolute alcohol Elemental analysis:

|  | % C | % H | % N |
|---|---|---|---|
| Calculated: | 58.97 | 6.67 | 8.97 |
| Found: | 58.59 | 6.72 | 8.96 |

Infrared spectrometry:

| 3400–2320 | cm⁻¹ | ν NH+ (hydrochloride) |
|---|---|---|
| 3040–2840 | cm⁻¹ | ν CH (alkyls) |
| 1670 | cm⁻¹ | ν CO (NCOS) |
| 1600 | cm⁻¹ | ν C=C (aromatics) |

Nuclear magnetic resonance spectrometry (80 MHz; DMSO-d₆):

| $\delta$ = 1.70 | ppm | (multiplet, 4H) | CH₂—CH₂—CH₂—CH₂ |
|---|---|---|---|
| $\delta$ = 2.00–2.75 | ppm | (multiplet, 4H) | CH₂—CH₂—CH₂—CH₂ |
| $\delta$ = 3.20–3.70 | ppm | (multiplet, 11H) | NCH₃ and piperazine |
| $\delta$ = 6.90–7.40 | ppm | (multiplet, 8H) | aromatic H |

EXAMPLE 30

3-Methyl-6-{2-[4-(2,4-Dichlorobenzyl) piperazin-1-yl)ethyl] benzothiazolinone

Reactants:
3-Methyl-6-(2-bromoethyl)benzothiazolinone: 0.0073 mol (2 g)
2,4-Dichlorobenzylpiperazine dihydrochloride: 0.0073 mol (2.3 g)
Triethylamine: 0.0150 mol (2cm³) Anhydrous acetone: 70 cm³
Procedure:
The procedure is identical to that used in Example 28, replacing 1-benzylpiperazine by 1-(2,4-dichlorobenzyl)piperazine.
Physicochemical data for the dihydrochloride:
Molecular weight: 509.26 g.mol⁻¹ for $C_{21}H_{25}Cl_4N_3OS$
Yield: 60%
Melting point: 189°–191° C.
Recrystallization solvent: Absolute alcohol Elemental analysis:

|  | % C | % H | % N |
|---|---|---|---|
| Calculated: | 49.52 | 4.94 | 8.25 |
| Found: | 49.37 | 5.05 | 8.27 |

Infrared spectrometry:

| 2940 | cm⁻¹ | ν CH (alkyls) |
|---|---|---|
| 2620–2180 | cm⁻¹ | ν NH+ (hydrochloride) |
| 1700 | cm⁻¹ | ν CO (NCOS) |
| 1580 | cm⁻¹ | ν C=C (aromatics) |

Nuclear magnetic resonance spectrometry (80 MHz; DMSO-d₆):

| $\delta$ = 3.60 | ppm | (multiplet, 2H) | CH₂—C₆H₃—Cl₂ |
|---|---|---|---|
| $\delta$ = 3.70 | ppm | (singlet, 3H) | NCH₃ |
| $\delta$ = 7.20–7.70 | ppm | (multiplet, 6H) | aromatic H |
| $\delta$ = 8.70 | ppm | (peak, 1H) | NH+ exchangeable in D₂O |
| $\delta$ = 10.85 | ppm | (peak, 1H) | NH+ exchangeable in D₂O |

EXAMPLE 31

3-Methyl-6-{4-[4-(2,4-Dichlorobenzyl) piperazin-1-yl)butyl] benzothiazolinone

Reactants:
3-Methyl-6-(4-bromobutyl)benzothiazolinone: 0.0066 mol (2 g)

2,4-Dichlorobenzylpiperazine dihydrochloride: 0.0066 mol (2.1 g)
Triethylamine: 0.0132 mol (1.80 cm$^3$)
Anhydrous acetone: 50 cm$^3$
Procedure:

The procedure is identical to that used in Example 29, replacing 1-benzylpiperazine by 1-(2,4-dichlorobenzyl)piperazine.

Physicochemical data (dihydrochloride):
Molecular weight: 537.31 g.mol$^{-1}$ for $C_{23}H_{29}Cl_4N_3OS$
Yield: 42%
Melting point: 257°–259° C.
Recrystallization solvent: Absolute alcohol

| Elemental analysis: | | | |
|---|---|---|---|
| | % C | % H | % N |
| Calculated: | 51.41 | 5.44 | 7.82 |
| Found: | 51.27 | 5.36 | 7.78 |

| Infrared spectrometry: | | |
|---|---|---|
| 3400–2360 | cm$^{-1}$ | ν NH+ (hydrochloride) |
| 3040–2840 | cm$^{-1}$ | ν CH (alkyls) |
| 1680 | cm$^{-1}$ | ν CO (NCOS) |
| 1580 | cm$^{-1}$ | ν C=C (aromatics) |

| Nuclear magnetic resonance spectrometry (80 MHz; DMSO-d$_6$): | | | |
|---|---|---|---|
| δ = 4.25 | ppm | (singlet, 2H) | CH$_2$—C$_6$H$_3$—Cl$_2$ |
| δ = 7.00–8.00 | ppm | (multiplet, 6H) | aromatic H |
| δ = 11.50 | ppm | (peak, 2H) | 2NH+ exchangeable in D$_2$O |

EXAMPLE 32

3-Methyl-6-{2-[4-(3,4-Dichlorobenzyl)piperazin-1-yl)ethyl] benzothiazolinone

Reactants:
3-Methyl-6-(2-bromoethyl)benzothiazolinone: 0.0073 mol (2 g)
3,4-Dichlorobenzylpiperazine dihydrochloride: 0.0073 mol (2.1 g)
Potassium carbonate: 0.029 mol (4 g)
Anhydrous acetone: 50 cm$^3$
Procedure:

The procedure is identical to that used in Example 29, replacing 1-benzylpiperazine by 1-(3,4-dichlorobenzyl)piperazine.

Physicochemical data for the dihydrochloride:
Molecular weight: 509.26 g.mol$^{-1}$ for $C_{21}H_{25}Cl_4N_3OS$
Yield: 56%
Melting point: >250° C.
Recrystallization solvent: Absolute alcohol

| Elemental analysis: | | | |
|---|---|---|---|
| | % C | % H | % N |
| Calculated: | 49.52 | 4.94 | 8.25 |
| Found: | 49.37 | 5.05 | 8.27 |

| Infrared spectrometry: | | |
|---|---|---|
| 2900 | cm$^{-1}$ | ν CH (alkyls) |
| 2300 | cm$^{-1}$ | ν NH+ (hydrochloride) |
| 1700 | cm$^{-1}$ | ν CO (NCOS) |
| 1590–1570 | cm$^{-1}$ | ν C=C (aromatics) |

| Nuclear magnetic resonance spectrometry (80 MHz; DMSO-d$_6$): | | | |
|---|---|---|---|
| δ = 2.80–3.15 | ppm | (multiplet, 12H) | ethylpiperazine |
| δ = 3.40 | ppm | (singlet, 3H) | NCH$_3$ |
| δ = 4.10 | ppm | (singlet, 2H) | CH$_2$—C$_6$H$_3$—Cl$_2$ |
| δ = 7.20–7.70 | ppm | (multiplet, 6H) | aromatic H |
| δ = 11.00 | ppm | (peak, 2H) | 2NH+ exchangeable in D$_2$O |

EXAMPLE 33

3-Methyl-6-{4-[4-(3,4-dichlorobenzyl)piperazin-1-yl)butyl] benzothiazolinone

Reactants:
3-Methyl-6-(4-bromobutyl)benzothiazolinone: 0.0033 mol (1 g)
3,4-Dichlorobenzylpiperazine dihydrochloride: 0.0033 mol (1 g)
Potassium carbonate: 0.0132 mol (1.8 g)
Anhydrous acetone: 40 cm$^3$
Procedure:

The procedure is identical to that used in Example 29, replacing 1-benzylpiperazine by 1-(3,4-dichlorobenzyl)piperazine.

Physicochemical data for the dihydrochloride:
Molecular weight: 537.31 g.mol$^{-1}$ for $C_{23}H_{29}Cl_4N_3OS$
Yield: 45%
Melting point (hydrochloride): >250° C.
Recrystallization solvent: Absolute alcohol

| Elemental analysis: | | | |
|---|---|---|---|
| | % C | % H | % N |
| Calculated: | 51.41 | 5.44 | 7.82 |
| Found: | 51.30 | 5.43 | 7.75 |

| Infrared spectrometry: | | |
|---|---|---|
| 3400–2360 | cm$^{-1}$ | ν NH+ (hydrochloride) |
| 3040–2960 | cm$^{-1}$ | ν CH (alkyls) |
| 1670 | cm$^{-1}$ | ν CO (NCOS) |
| 1600 | cm$^{-1}$ | ν C=C (aromatics) |

| Nuclear magnetic resonance spectrometry (80 MHz; DMSO-d$_6$): | | | |
|---|---|---|---|
| δ = 1.40–1.80 | ppm | (multiplet, 4H) | CH$_2$—CH$_2$—CH$_2$—CH$_2$ |
| δ = 4.20 | ppm | (singlet, 2H) | CH$_2$—C$_6$H$_3$—Cl$_2$ |
| δ = 7.00–8.00 | ppm | (multiplet, 6H) | aromatic H |
| δ = 11.25 | ppm | (peak, 2H) | 2NH+ exchangeable in D$_2$O |

EXAMPLE 34

6-{3-[4-(2-Methoxy-phenyl)piperazin-1-yl]propyl} benzothiazolinone

Melting point (hydrochloride): 224°–225 ° C.

EXAMPLE 35

3-Methyl-6-{3-[4-(2-Methoxy-phenyl)piperazin-1-yl)propyl] benzothiazolinone

Melting point (hydrochloride): 205°–207° C.

PHARMACOLOGICAL STUDY OF THE COMPOUNDS OF THE INVENTION

EXAMPLE A

Study of the Acute Toxicity

The acute toxicity was evaluated after oral administration of a dose of 100 mg.kg$^{-1}$ of the compounds of the invention to batches of 8 mice (26±2 grams). The animals were observed at regular intervals during the first day and daily for the two weeks following the treatment.

The compounds of the invention appear to be totally non-toxic. They cause no deaths after administration of a dose of 100 mg.kg$^{-1}$ and no disorders are observed after administration of this dose.

EXAMPLE B

In Vitro Receptor Affinity Analysis

The products are tested on each receptor at 5 different concentrations ($10^{-5}$M, $10^{-6}$M, $10^{-7}$M, $10^{-8}$M, $10^{-9}$M) in triplicate. When the binding coefficient IC$_{50}$ is below a concentration of $10^{-6}$M, the Ki is measured using 12 concentrations of the product.

The Table below presents the receptors whose affinity for the compounds of the invention was determined, the tissue chosen, the concentration selected to determine the non-specific binding and the radioligand used to label the receptor.

Moreover, the compounds of the present invention are also much more selective than the compounds of Application EP 478,446. In particular, they have 100 to 1000 times less affinity for the D$_2$ receptors than do the compounds of Application EP 478,446.

EXAMPLE C

Antagonism of the Hypermotility Induced by Amphetamine

Groups of 10 NMRI-CERJ mice are injected intraperitoneally (IP) with 4 mg/kg$^{-1}$ of d-amphetamine immediately after IP injection of the compound to be tested, and the mice are placed in an actimeter for 30 minutes.

The number of interruptions of the photoelectric cells is counted, as is the stereotyped behavior.

The activity of the compounds tested is expressed as a percentage of the antagonism of the hyperactivity induced by amphetamine. The compounds of the invention are powerful antagonists of the hypermotility induced by amphetamine, which makes it possible to arrive at an activity in disorders of the central nervous system for the products of the invention.

EXAMPLE D

Investigation into the Catalepsigenic Effect

The catalepsigenic effect is investigated in rats via the intraperitoneal route. This test predicts the existence of side effects of extrapyramidal type. 6 groups of Wistar rats

| Receptor or site | Radioligand | Non-specific binding | Tissue |
|---|---|---|---|
| 5-HT$_{1A}$ | [$^3$H]8-OH DPAT | $10^{-5}$ M Buspirone | Bovine hippocampus + frontal cortex |
| 5-HT$_{1B}$ | [$^3$H] Cyanopindolol or 5-OH tryptamine or propanolol | $10^{-5}$ M Cold serotonin | Rat brain + frontal cortex + striatum |
| 5-HT$_{1C}$ | [$^3$H]N-methyl mesulergine | $10^{-5}$ M Mianserin | Pig choroid plexus |
| 5-HT$_2$ | [$^3$H] ketanserin | $10^{-5}$ M Spiperone | Bovine frontal cortex |
| 5-HT$_3$ | [$^3$H] Quipazine or BRL 93694 | $10^{-5}$ M ICS 255930 | NG 108-15 cells |
| α$_1$ | [$^3$H] Prazosin | $10^{-5}$ M Phentolamine | Rat brain |
| α$_2$ | [$^3$H] Rauwolscine | $10^{-5}$ M Yohimbine | Rat brain |
| D$_1$ | [$^3$H] SCH 23390 | $10^{-6}$ M Butaclamol | Bovine striatum |
| D$_2$ | [$^3$H] Raclopride | $10^{-6}$ M spiperone or $10^{-6}$ M Haloperidol | Bovine stratum |
| M$_1$ | [$^3$H] Telenzepine | $10^{-5}$ M Atropine | Rat cortex |
| H$_1$ | [$^3$H] Pyrilamine | $10^{-6}$ M Chloropheniramine | Calf cortex |
| σ | [$^3$H] | $10^{-6}$ M 3-PPP | Calf hippocampus |

The results of the test showed that the compounds of the invention are powerful and selective ligands for the σ receptors. By way of comparison, the compounds of the present invention have an affinity which is 100 to 1000 times stronger than that of the compounds of Application EP 478,466 for the sigma receptor, and more particularly Examples 28 to 32 and 172 of this Application, which are structurally the most similar to those of the present invention.

received an injection of the compounds of the invention and were then tested for their catalepsigenic activity after a 30-minute interval. Haloperidol is used as reference.

The results show that the compounds of the invention are very low in catalepsigenic power when compared with haloperidol which produces, at a dose of 2 mg.kg$^{-1}$, a catalepsigenic effect of 95% under the same study conditions. This result confirms the absence of side effects of extrapyramidal type for the products of the invention which might be expected following on from the receptor binding results (Example B).

EXAMPLE E

Study of the Antidepressant Activity of the Compounds of the Invention

PRINCIPLE:

The product study is based on the "acquired refusal" model which consists in inducing in the animal, by means of a series of uncontrollable aversive events, a deficit during subsequent avoidance tests.

Protocol:

This test was developed by Sherman A. D., Sacquitne J. L., and Petty F. (Pharmacol. Biochem. Behav., 1982, 16, 449–454). We use male Wistar rats weighing between 180 and 200 grams. The animals are kept in the animal house one week before the test, in plastic boxes, in groups of 10, at an ambient temperature of 21° C.±1° C., with free access to water and food.

The animals are then isolated in small boxes and are subjected to 60 unavoidable electric shocks (0.8 mA every minute±15 seconds). A control group of rats receives no electric shocks.

The avoidance learning capacity of the animals (passage from one compartment to the other in order to avoid the electric shocks) is evaluated 48 hours later and for 3 consecutive days. During the learning sessions, the animals undergo 2 tests per minute for 15 minutes. The number of avoidance failures is noted for each rat. The animals are treated (i.p.: 0.5 cm$^3$/100 g) on an empty stomach 6 hours after the unavoidable shocks and for 4 consecutive days, in the morning 30 minutes before the learning session and in the evening between 6 and 7 pm.

The test products are dissolved in distilled water.

The test products are administered at doses of 0.05 mg.kg$^{-1}$/day.

Results:

The test proves that the products of the invention significantly reduce the number of avoidance failures, which reflects, for some products of the invention, a strong activity of antidepressant type.

EXAMPLE F

Study of the Anxiolytic Activity—So-called Light/Dark Cage Test in Mice

Principle:

A study of the anxiolytic effects of the compounds of the invention is proposed, by means of the light/dark cage test in mice.

Protocol:

This test was developed by Crawley et al. (1981, Pharmacol. Biochem. Behav.), and then modified and behaviorally validated.

The test involves two cages of equal size (20×20×14 cm) made of PVC. One is brightly lit with a 100 W lamp ("cold" light), the other is darkened. The two cages are separated from each other by means of a small opaque tunnel (5×7 cm). The mice are introduced individually into the dark cage and the time spent by the animals in the lit cage, as well as the number of transitions between the dark cage and the lit cage, are recorded by means of keyboards connected to a computer, over 5 minutes.

Each experimental group comprises at least 15 animals.

Results:

The intraperitoneal administration of some of the products of the invention results in an increase in the time spent by the mice in the lit cage and in the number of transitions between the lit cage and the dark cage.

This significant increase in the two parameters studied shows the noteworthy anxiolytic activity of certain compounds of the invention.

EXAMPLE G

Investigation into an Antiarthritic-type Activity in Rats

Groups of 5 male or female Lewis rats weighing 130 to 150 g are used. A suspension of 0.3 mg of killed *Mycobacterium tuberculosis* in 0.1 cm$^3$ of mineral oil (complete Freund adjuvant, CFA) is administered into the subplantar region of the right hind foot on day 1. The volumes of the hind feet are measured by displacement of water on days 0, 1, 5, 14 and 18. The rats are weighed on days 0 and 18. The products to be tested are suspended in carboxymethylcellulose and are administered orally for 5 consecutive days from days 1 to 5.

In parallel, a control group is used in order to eliminate artefacts resulting from the handling of the animals. A group treated with a reference product permits validation of the test.

At a dose of 10 mg.kg$^{-1}$, the products of the invention allow an inhibition in the increase in volume of the foot in the late phase of the inflammation (days 14 to 18).

EXAMPLE H

Pharmaceutical Composition Intended for the Treatment of Disorders of the Central Nervous System Tablets containing a 0.1 mg dose of 3-methyl-6-[2-(4-benzylpiperazin-1-yl)ethyl] benzothiazolinone.

Formula for 10,000 tablets:
3-Methyl-6-[2-(4-benzylpiperazin-1-yl)ethyl]benzothiazolinone 1 g
Wheat starch 75 g
Corn starch 75 g
Lactose 325 g
Magnesium stearate 10 g
Silica 5 g
Hydroxylpropylcellulose 10 g

EXAMPLE I

Pharmaceutical Composition

Tablets containing a 0.1 mg dose of 6-(3-morpholinopropyl)benzothiazolinone.

Formula for 10,000 tablets:
6-(3-Morpholinopropyl)benzothiazolinone 1 g
Wheat starch 75 g
Corn starch 75 g
Lactose 325 g
Magnesium stearate 10 g
Silica 5 g
Hydroxylpropylcellulose 10 g

We claim:
1. A compound selected from those of formula (I):

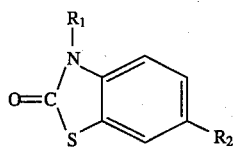

in which:

R₁ represents hydrogen or alkyl or substituted alkyl,
and R₂ represents a group of formula R₂₁:

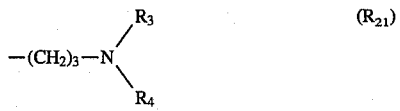

in which:

R₃ and R₄ together form a saturated 5- to 9-membered heterocycle which may contain other hetero atoms chosen from oxygen and sulfur and which may be unsubstituted or substituted or 4-(methoxyphenyl)-piperazin-1-yl, or a group of formula R₂₂:

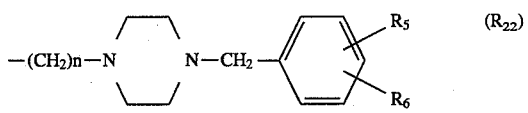

in which n represents 2, 3 or 4, and R₅ and R₆, which are identical, represent hydrogen or halogen, it being understood that in the formula (I), the term "substituted" associated with the heterocycle formed by —NR₃R₄ means that the substitution may be made by one or more alkyl, the terms "alkyl" and "alkoxy" denote linear or branched groups containing 1 to 6 carbon atoms inclusive, an optical isomer thereof, and an addition salt thereof with a pharmaceutically-acceptable acid or, when R₁ represents hydrogen, an addition salt thereof with a pharmaceutically-acceptable base.

2. A compound of claim 1 selected from 6-(3-morpholinopropyl) benzothiazolinone and an addition salt thereof with a pharmaceutically-acceptable acid.

3. A compound of claim 1 selected from 3-methyl-6-(3-morpholinopropyl) benzothiazolinone and an addition salt thereof with a pharmaceutically-acceptable acid.

4. A compound of claim 1 selected from 3-methyl-6-{2-[4-(2,4-dichlorobenzyl) piperazin-1-yl)ethyl]benzothiazolinone and an addition salt thereof with a pharmaceutically-acceptable acid.

5. A compound of claim 1 selected from 3-methyl-6-{2-[4-(3,4-dichlorobenzyl)piperazin-1 -yl)ethyl]benzothiazolinone and an addition salt thereof with a pharmaceutically-acceptable acid.

6. A compound of claim 1 selected from 3-methyl-6-[4-(4-benzylpiperazin-1-yl) butyl]benzothiazolinone and an addition salt thereof with a pharmaceutically-acceptable acid.

7. A compound of claim 1 selected from 3-methyl-6-[2-(4-benzylpiperazin-1-yl)ethyl] benzothiazolinone and an addition salt thereof with a pharmaceutically-acceptable acid.

8. A pharmaceutical composition useful as an antipsychotic containing an effective amount of a compound of claim 1 or an addition salt thereof with a pharmaceutically-acceptable acid or, where appropriate, with a pharmaceutically-acceptable base, in combination with one or more excipients.

9. A method of treating a mammal afflicted with a disease associated with sigma receptors comprising the step of administering to the said mammal an amount of a compound of claim 1 which is effective for alleviation of the said disease.

10. A method of claim 9 wherein the disease is a psychiatric disease.

* * * * *

UNITED STATES PATENT AND TRADEMARK OFFICE
CERTIFICATE OF CORRECTION

PATENT NO. : 5,512,569
DATED : April 30, 1996
Page 1 of 3
INVENTOR(S) : Hamid A. Mansour; Thierry Taverne; Raymond Houssin; Isabelle Lesieur; Patrick Depreux; Gerard Adam; Daniel-Henri Caignard; Pierre Renard; Marie-Claire Rettori It is certified that error appears in the above-indentified patent and that said Letters Patent is hereby corrected as shown below:

Title Page, [75], Inventors: "Geard Adam" should read -- Gerard Adam --.

Title Page, Other Publications, 12th line from top: "Atyptical" should read -- Atypical --. See Foreign Patent Documents, PTO 1449, Other Prior Art Column 1, line 6: Delete the "-" (dash) at the end of the line and insert -- ) --.

Column 1, line 7: Delete the ")" at the beginning of the line.

Column 6, line 35: Insert -- : -- after "weight".

Column 9, line 2: "aminopropyl)" should read -- aminopropyl] --.

Column 9, line 11: "aminopropyl)" should read -- aminopropyl] --.

Column 9, line 62 (approx.): "aminopropyl" should read -- aminopropyl] --.

UNITED STATES PATENT AND TRADEMARK OFFICE
CERTIFICATE OF CORRECTION

PATENT NO. : 5,512,569
DATED : April 30, 1996
Page 2 of 3
INVENTOR(S) : Hamid A. Mansour; Thierry Taverne; Raymond Houssin; Isabelle Lesieur; Patrick Depreux; Gerard Adam; Daniel-Henri Caignard; Pierre Renard; Marie-Claire Rettori It is certified that error appears in the above-indentified patent and that said Letters Patent is hereby corrected as shown below:

Column 12, line 19 (approx.): "piperazin-1-yl)ethyl]" should read -- piperazin-1-yl]ethyl} --.

Column 12, line 26: "Anhydrous...." should begin a new line.

Column 12, line 63 (approx.): "piperazin-1-yl)butyl]" should read -- piperazin-1-yl]butyl} --.

Column 13, line 37 (approx.): "piperazin-1-yl)ethyl]" should read -- piperazin-1-yl]ethyl} --.

Column 14, line 15: "piperazin-1-yl)butyl]" should read -- piperazin-1-yl]butyl} --.

Column 14, lines 64 & 65: "piperazin-1-yl)propyl]" should read -- piperazin-1-yl]propyl} --.

Column 15, line 52 (approx.): "stratum" should read -- striatum --.

Column 15, line 58 (approx.): "[$^3$H]" should read -- [$^3$H] DTG --.

UNITED STATES PATENT AND TRADEMARK OFFICE
CERTIFICATE OF CORRECTION

PATENT NO. : 5,512,569

DATED : April 30, 1996

INVENTOR(S) : Hamid A. Mansour; Thierry Taverne; Raymond Houssin; Isabelle Lesieur; Patrick Depreux; Gerard Adam; Daniel-Henri Caignard; Pierre Renard; Marie-Claire Rettori It is certified that error appears in the above-indentified patent and that said Letters Patent is hereby corrected as shown below:

Column 17, line 37: "mg.kg" should read -- $mg.kg^{-1}$/ --.

Column 17, line 38: Delete "$_1$/" from beginning of line.

Column 20, line 11 (approx.): "piperazin-1-yl)ethyl]" should read -- piperazin-1-yl]ethyl}.

Column 20, line 15: "piperazin-1-yl)ethyl]" should read -- piperazin-1-yl]ethyl} --.

Signed and Sealed this

Tenth Day of September, 1996

BRUCE LEHMAN

*Attest:*

*Attesting Officer*   Commissioner of Patents and Trademarks